United States Patent
Campesi, Sr.

(10) Patent No.: US 6,676,033 B1
(45) Date of Patent: Jan. 13, 2004

(54) SYSTEM FOR DISPENSING ANIMAL SCENT ATTRACTANT

(76) Inventor: Ross J. Campesi, Sr., 52410 Clark Rd., White Castle, LA (US) 70788-4914

( * ) Notice: Subject to any disclaimer, the term of this patent is extended or adjusted under 35 U.S.C. 154(b) by 79 days.

(21) Appl. No.: 09/892,673

(22) Filed: Jun. 27, 2001

(51) Int. Cl.$^7$ ................................................ A24F 25/00
(52) U.S. Cl. .............................. 239/44; 239/47; 239/50
(58) Field of Search ............................. 239/43, 44, 47, 239/48, 50, 38, 145; 43/1, 44.9, 44.91; 431/320

(56) References Cited

U.S. PATENT DOCUMENTS

| | | | | |
|---|---|---|---|---|
| 2,983,067 A | * | 5/1961 | Saywell, Jr. .................. | 43/44.9 |
| 3,701,212 A | * | 10/1972 | Gilliam ........................ | 43/44.9 |
| 4,268,988 A | * | 5/1981 | Johnson, Jr. II ............ | 43/43.11 |
| 4,546,567 A | * | 10/1985 | Bailey ......................... | 43/44.9 |
| 4,964,744 A | * | 10/1990 | Whitear ...................... | 239/48 |
| 5,048,218 A | * | 9/1991 | Stewart ........................... | 43/1 |
| 5,622,314 A | * | 4/1997 | Eason .......................... | 239/44 |
| 5,832,648 A | * | 11/1998 | Malone ....................... | 239/47 |
| 5,938,430 A | * | 8/1999 | Majerowski ................ | 431/320 |
| 5,947,379 A | | 9/1999 | Freeman | |

* cited by examiner

*Primary Examiner*—Dinh Q. Nguyen
(74) *Attorney, Agent, or Firm*—Jones, Walker, Waechter, Poitevent, Carrere & Denegre, L.L.P.

(57) ABSTRACT

A dispenser system for scented material for use during hunting includes a container having a sealable opening and a wick stored in the container, the wick having a series of weights distributed thereon. The wick may have a tab positioned on one end to prevent complete removal of the wick from the bottle, and a grab hook at the other end. The dispenser system may include an auxiliary line attachable to the grab hook for connecting the wick to a tree limb of the like.

13 Claims, 1 Drawing Sheet

SYSTEM FOR DISPENSING ANIMAL SCENT ATTRACTANT

FIELD OF THE INVENTION

The invention relates to a container for storing and dispensing game animal scent attractant, particularly game animal urine, such as deer urine.

BACKGROUND OF THE INVENTION

Hunters employ many techniques to lure game animals such as deer to a desired hunting area. One technique is deploying animal scent in the hunt area. The scents used include urine from the hunted animal, or estrus scent. Such scented lures are typically available as liquid concentrates.

The concentrated scent may be dispensed at the hunt site in many ways. Typically, the scent is stored in a sealed container and dispensed from the container at the hunt site, such as by applying the scent to an elevated scent pad disposed in an artificial scrape surrounding an artificial rub. Alternatively, a scent container may contain a wick stored in the container and soaked in the scent. At the hunt site, the wick is deployed from the container and suspended from a tree or bush. One end of the wick may have a hook to assist deployment, while the other end may be attached to a device to prevent complete separation from the container. At the end of the hunt, the wick is then restored into the container.

With these containers, re-storage of the wick is problematic. Many of the scents have an odor that is pungent to humans and difficult to remove from skin and clothing; therefore great care is required in handling the wick, as it is difficult to re-store the wick without the user's hands contacting the wick and scent. One approach to solve this problem was to incorporate a reel internally into the container with an external crank, thereby allowing the wick to be withdrawn into the container without the need to handle the wick. One such device is shown in U.S. Pat. No. 5,947,379 to Freeman, hereby incorporated by reference.

This design however has a tendency to be complex, expensive to make, and subject to leakage, as the container is usually manufactured in two mating halves, and the container further has a number of gaskets used to seal off the various compartments.

SUMMARY OF THE INVENTION

Accordingly, it is an object of the invention to provide a container for scented materials for use during hunting which provides compact storage, does not leak, and has a wick easily retractable into the container.

To that end, a dispenser system for storing and deploying scented material for use during hunting is provided which includes a container having a sealable opening and a wick stored in the container, the wick having a series of weights distributed thereon. The wick may have a tab positioned on one end to prevent complete removal of the wick from the bottle, and a grab hook at the other end. The dispenser system may include an auxiliary line attachable to the grab hook for connecting the wick to a tree limb or the like.

DESCRIPTION OF THE PREFERRED EMBODIMENTS

Figures 1A, 1B:
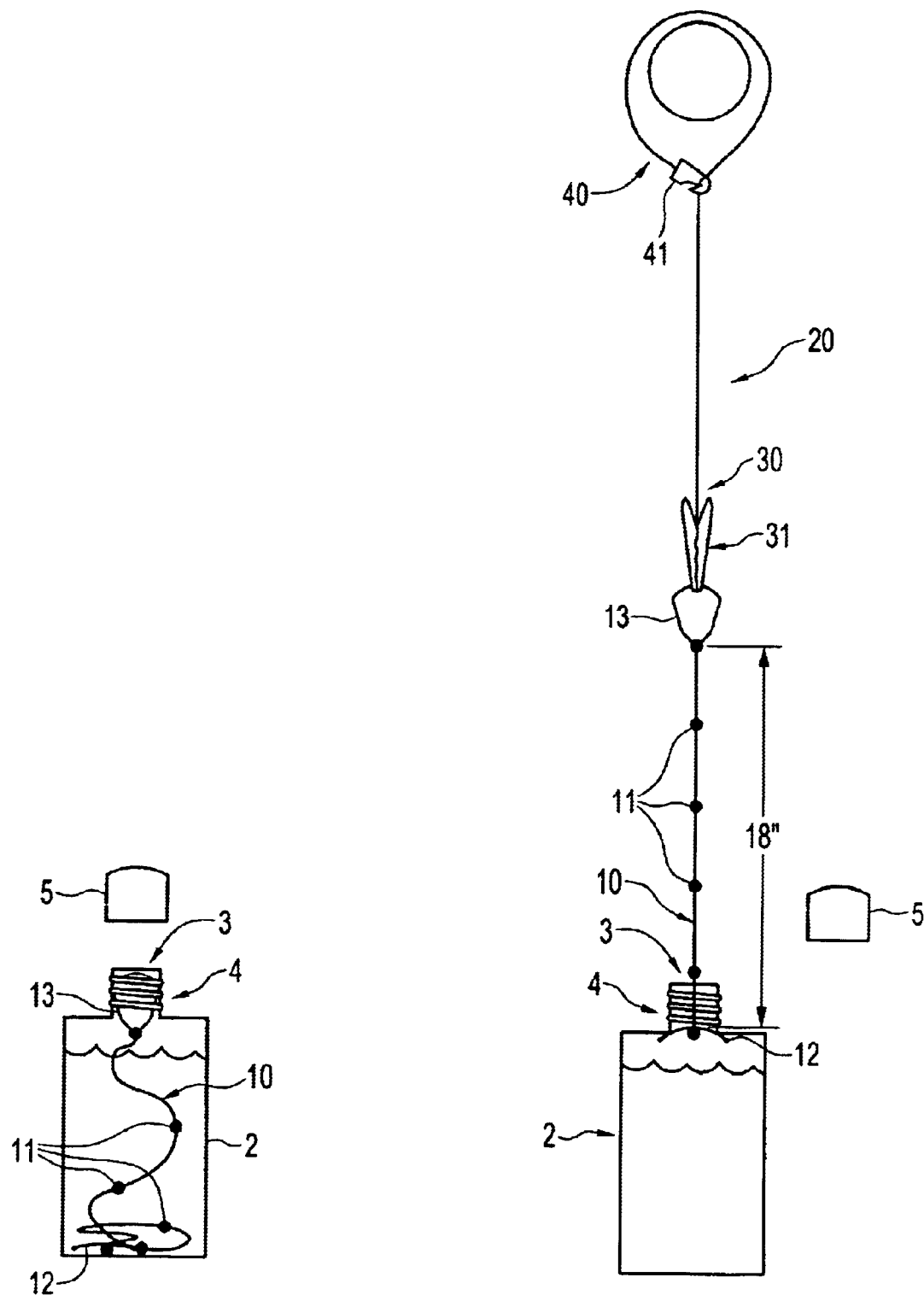
FIG. 1a is a schematic showing the container and wick stored in the container.
FIG. 1b is a schematic showing the container, wick and auxiliary line after deployment.

As shown in FIG. 1a, the system includes a container 2. As shown, container 2 is a plastic bottle having an opening 3 defined by a neck 4. It is preferred that the container 2 be inert to the materials stored in the container, such as deer urine. The opening 3 is sealingly closable through use of cap 5 and the cap 5 may include an optional gasket. As shown, the cap 5 engages the bottle's neck 4 through the action of matching threads. Container 2 is sized to be easily transportable and preferably, fit in a shirt pocket.

The system also includes a wick 10. Wick 10 is a length of wickable, or more generally, wetable fabric, such as cotton, and is stored in the interior of the container 2. One source of a suitable wick 10 is round shoestring. Placed along the length of the wick 10 is at least one weight, with a plurality of weights 11 preferred. One type of weight found suitable is fishing line weight crimped onto the wick. As shown, weights are placed on the wick 10 at intervals of 2–3 inches, using 1–3 ounce weights.

One end of the wick 10 has attached thereto a tab 12. The tab 12 should be larger in at least one dimension then the diameter of the opening 3. In this fashion, it is possible to insert the tab 12 with wick attached into the interior of the container 2, but because of the tab's size, it is difficult to remove the tab 13 from the interior of the container 2. One type of tab 12 is a portion of a paper clip. Flexible plastic tabs could also be used, where the tab is "flexed" for insertion. Another embodiment may have one end of the wick attached to the interior of the container, such as with glue or the like, thereby preventing full removal of the wick from the interior of the container.

Attached to the other end of the wick 10 is a grab hook 13. Grab hook 13, as shown, is a loop made from a paper clip. Grab hook 13 is designed to be grabbed (by the hands or other suitable implement) and pulled out of the interior, thereby deploying the wick 10. Grab hook 13 should have one dimension slightly greater than the diameter of the opening 3 so that the grab hook 13 will not fall into the interior of the container 2. It is not necessary that the grab hook 13 be "hooked" or "looped" shaped. For instance, the grab hook 13 could be a bar attached to the end of the wick, or a knot formed in the end of the wick 10, where the knot is slightly larger in size than the container opening. It is desired that the grab hook 13 be insertable into the neck 4 of the container 2, to allow the cap 5 to close and seal over the grab hook 13. Consequently, it is preferred that either the neck 4 of the container 2 or the grab hook 13 (or both) be slightly flexible.

Additionally, the system may have a auxiliary line 20, shown in FIG. 1b. Auxiliary line 20 has two ends, a first end 30 and a second end 40. First end 30 has a device 31 or a means for engaging the grab hook on the wick, to assist in removal and re-insertion of the wick. Device 31 may be a hook, clasp, clip, (shown is an alligator clip) or a loop of Velcro. Second end 40 may be attached to a tree or brush limb, and can include a hook 41 to assist in so attaching. Auxiliary line 20 can made from a non-wickable material, as the auxiliary line 20 is not intended to be stored in the interior of the container 2.

One end of the wick 10 has attached thereto a tab 12. The tab 12 should be larger in at least one dimension then the diameter of the opening 3. In this fashion, it is possible to insert the tab 12 with wick attached into the interior of the container 2, but because of the tab's size, it is difficult to remove the tab 12 from the interior of the container 2. One type of tab 12 is a portion of a paper clip. Flexible plastic tabs could also be used, where the tab is "flexed" for insertion. Another embodiment may have one end of the wick attached to the interior of the container, such as with glue or the like, thereby preventing full removal of the wick from the interior of the container.

Attached to the other end of the wick 10 is a grab hook 13. Grab hook 13, as shown, is a loop made from a paper clip. Grab hook 13 is designed to be grabbed (by the hands or other suitable implement) and pulled out of the interior, thereby deploying the wick 10. Grab hook 13 should have one dimension slightly greater than the diameter of the opening 3 so that the grab hook 13 will not fall into the interior of the container 2. It is not necessary that the grab hook 13 be "hooked" or "looped" shaped. For instance, the grab hook 13 could be a bar attached to the end of the wick, or a knot formed in the end of the wick 10, where the knot is slightly larger in size than the container opening. It is desired that the grab hook 13 be insertable into the neck 4 of the container 2, to allow the cap 5 to close and seal over the grab hook 13. Consequently, it is preferred that either the neck 4 of the container 2 or the grab hook 13 (or both) be slightly flexible.

Additionally, the system may have a auxiliary line 20, shown in FIG. 1b. Auxiliary line 20 has two ends, a first end 30 and a second end 40. First end 30 has a device 31 or a means for engaging the grab hook on the wick, to assist in removal and re-insertion of the wick. Device 31 may be a hook, clasp, clip, (shown is an alligator clip) or a loop of Velcro. Second end 40 may be attached to a tree or brush limb, and can include a hook 41 to assist in so attaching. Auxiliary line 20 can made from a non-wickable material, as the auxiliary line 20 is not intended to be stored in the interior of the container 2.

In use, the cap 5 is removed and scent is poured into the container. The cap 5 is then replaced, and the container 2 taken to the hunt site. At the hunt site, the cap 5 is removed and the grab hook 13 of the wick 10 is grasped and pulled, drawing out the wick 10. The auxiliary line 10 can be used to accomplish the grasping, if desired (shown in FIG. 1b). The grab hook 13 (or the second end of the auxiliary line if the auxiliary line is utilized) is then attached to a tree limb or the like, suspending the saturated wick 10 in the air at a suitable height. The container 2 should also be suspended in the air to prevent the contents from spilling. At the end of the hunt, the grab hook 13 (or the second end of the auxiliary line) is detached from the tree limb or the like, and the wick 10 is threaded back into the interior of the container 2. The weights 11 greatly assist re-insertion of the wick 10, as the weights 11 help maintain the exposed portion of the wick 10 under tension, allowing the operator to simply lower the wick 10 into the interior, or if need be, to steer the wick 10 into the interior. Because the wick 10 is under tension, the wick 10 will generally follow a straight line into the interior and not flop about upon re-insertion.

I claim:

1. A dispensing system for dispensing animal scent comprising a container system including a container having an interior and an opening into said interior, said opening being sealable, said container system furthers having a wick, said wick having a top portion and a bottom portion and a portion intermediary said top and said bottom portion, said container system further having a series of weights positioned on said wick, at least one of said series of weights positioned on said intermediary portion of said wick; said dispensing system further having an auxiliary line, said auxiliary line attachable to said container system.

2. The dispersing system of claim 1 where said container system further has a tab positioned on said bottom portion of said wick, said tab adapted to resist removal of said tab through said opening.

3. The dispensing system according to claim 1 wherein said container system further has a cap for sealing said opening of said container.

4. The dispensing system according to claim 3 wherein said auxiliary line is removably attachable to said container system.

5. The dispensing system according to claim 1 wherein said container has a neck forming said opening.

6. The dispensing system according to claim 1 further having a grab hook, said grab hook positioned on said top portion of said wick, said grab hook sized to resist insertion of id grab hook through said opening into said interior of said container.

7. The dispensing system according to claim 6 wherein said auxiliary line is removably attachable to said grab book or said wick.

8. The dispensing system according to claim 6 wherein said auxiliary line has a first and a second end, said first end having a means for engaging said grab hook.

9. The dispensing system according to claim 8 where said second end of said auxiliary line has a hook positioned thereon.

10. The dispensing system according to claim 6 where said grab hook is a loop.

11. The dispensing system according to claim 1 wherein said weights are crimped onto said wick.

12. The dispensing system according to claim 1 wherein said weights are within the range of 0.5 to 3 ounces.

13. The dispensing system according to claim 1 wherein said bottom portion of said wick is being fixedly attached to said interior of said container.

* * * * *